United States Patent [19]

Weil et al.

[11] Patent Number: 5,656,628
[45] Date of Patent: Aug. 12, 1997

[54] USE OF L-ACETYLCARNITINE FOR THE TREATMENT OF AIDS

[75] Inventors: Roger Weil, Geneva, Switzerland; Laura Scandurra, Viagrande, Italy

[73] Assignee: ZW Biomedical Research AG, Bern, Switzerland

[21] Appl. No.: 364,711

[22] Filed: Dec. 27, 1994

(Under 37 CFR 1.47)

Related U.S. Application Data

[63] Continuation of Ser. No. 263,040, Jun. 21, 1994, abandoned.

[30] Foreign Application Priority Data

Jun. 21, 1993 [CH] Switzerland ............ 1838/93

[51] Int. Cl.$^6$ ............ A61K 31/535; A61K 31/35
[52] U.S. Cl. ............ 514/228.8; 514/451; 514/459; 514/556; 514/931; 514/934; 514/967; 514/969; 424/430; 424/433; 424/436
[58] Field of Search ............ 424/433, 430, 424/436; 514/556, 931, 934, 967, 969, 228.8, 451, 459

[56] References Cited

U.S. PATENT DOCUMENTS

4,415,588  11/1983  Cavazza ............ 424/311
5,314,689  5/1994  Scandurra et al. ............ 424/433

OTHER PUBLICATIONS

De Simone, C., et al., Acetyl–L Carnitine as a Modulator of the Neuro–Endocrine—Immune Interaction in HIV + Subjects. Excerpta Medica, Amsterdam (1989) 128: 125–138.

De Simone, C, et al., Amelioration of the Depression of HIV—Infected Subjects with L–Acetyl Carnitine Therapy. J Drug Dev, (1988) 1(3): 163–166

De Simone, C., et al., High Dose L–Carnitine Improves Immunologic and Metabolic Parameters in AIDS Patients. Immunopharmacology and Immunotoxicology (1993) 15 (1): 1–12.

*Primary Examiner*—Nathan M. Nutter
*Attorney, Agent, or Firm*—John P. White

[57] ABSTRACT

This invention relates to the use of L-acylcarnitine for the preparation of a drug and a technique for relieving the disease symptoms appearing in AIDS by administering an L-acylcarnitine. The invention furthermore relates to a drug for this purpose, characterized in content by L-acylcarnitine as active principle. The preferred L-acylcarnitine is L-acetylcarnitine.

7 Claims, No Drawings

USE OF L-ACETYLCARNITINE FOR THE TREATMENT OF AIDS

This application is a continuation of U.S. Ser. No. 08/263,040, filed Jun. 21, 1994 and now abandoned and claims the benefit of that application under 35 U.S.C. §120. U.S. Ser. No. 08/263,040 claims priority under 35 U.S.C. §119 of Swiss application No. 1838/93 filed Jun. 21, 1993.

The present invention relates to a new drug for relieving the physical complaints appearing in AIDS infections.

It was assumed for a long time that a pure virus infection was involved in AIDS diseases in which HIV viruses, among which two types (HIV 1 and HIV 2) could be identified and isolated up to now, mainly cause immune deficiency in the human defense system so that after the disease has appeared, the patient involved is rendered defenseless against all infections induced by other pathogens.

More recent research has led to the conviction that said viruses indeed causally participate in the disease and especially in its transmission, but that still other not yet completely clarified mechanisms of very complicated type play a substantial part in this hitherto incurable disease. Reference is made in this connection, among others, to the publications of Bernhard Hirschel, "AIDS", 1992, Hans Huber, pub., Bern, and Vincent T. DeVita et al., "AIDS", third edition, 1992, J. B. Lippincott Co., Philadelphia. It is known that a patient infected with HIV has this infection for 5–10 years, and only then do the severe clinical symptoms of AIDS diseases appear, which usually lead relatively rapidly to death.

Disease symptoms very often encountered in AIDS patients, and which render them unfit to work for longer or shorter periods, are described in detail in the above publications. The disease course and symptoms are assessed there in detail.

The object of the present invention was to develop an effective agent capable of relieving physical symptoms in AIDS patients.

It was now surprisingly found that the physical complaints could be relieved, at least to the extent of making patients feel well and again completely perform their earlier work in a surprisingly short time and to a very satisfactory degree, by administration of an L-acylcarnitine.

The present invention relates to the use of L-acylcarnitine for the preparation of a drug and a technique for relieving the disease symptoms appearing in AIDS by administering an L-acylcarnitine. The invention furthermore relates to a drug for this purpose, characterized by a content in L-acylcarnitine as active principle.

The invention is defined in the independent claims. Preferred forms of execution are contained in the subordinate claims.

The preferred L-acylcarnitine is L-acetylcarnitine, a compound contained in the human body, whose synthetic preparation is also known, freely available on the market, which does not induce any kind of known undesired side effects, and which is known as a drug for other purposes. For example, it has been proposed for oral use in the treatment of age-conditioned neurologic and metabolic disorders, such as loss of memory, behavioral disturbances, and erratic phenomena, such as appear in senile dementia. In addition, the effect of L-acetylcarnitine on depressions in HIV-infected patients was investigated; moreover, bromoacetylcarnitine was proposed for controlling trypanosomes, and an antitumoral effect was ascribed to palmitoylcarnitine. The use of L-acylcarnitine as an antiviral agent was already also proposed; very good results were obtained in the treatment and prevention of virus infections, especially with the topical application of L-acetylcarnitine.

It was not at all to be expected, on the basis of the state of the art, that L-acylcarnitine could also be introduced for the treatment of physical disease symptoms in AIDS patients.

The treatment is generally oral, preferably in does of 25–30 mg/kg of body weight/day. L-Acetylcarnitine can be administered in the form of tablets, effervescent powder, dragees, solutions, syrup, etc., preferably in two doses, in each case after breakfast and lunch. The mechanism of action has not yet been clarified.

Clinical experiments on a larger scale are underway. Their results will be presented later.

EXAMPLE

Sachets containing 500 mg active principle are prepared in a usual way from a mixture of 590 mg L-acetylcarnitine hydrochloride with the excipients usual for an effervescent powder.

Tablets with 500 mg active principle can be prepared in a usual way from 590 mg L-acetylcarnitine with the corresponding tablet adjuvant materials.

Two volunteer patients were treated with these preparations as follows:

Case 1

Male volunteer, 47 years old.

Diagnosis: AIDS infection through blood transfusion (Walter Reed 6), probably infected in March, 1984.

Prior treatment: with AZT for 90 days; treatment suspended due to side effects.

Treatment: 25 mg/kg/day L-acetylcarnitine since Apr. 15, 1991, without interruption.

History:

The primary infection ran without symptoms. Detection of the infection took place in December, 1990. The symptoms were as described below.

The following clinical and laboratory findings were obtained at the beginning of the treatment with L-acetylcarnitine:

weight: 75 kg;

bilaterally swollen lymph glands in the lateral and posterior cervical region, the axilla area, and the inguinal regions;

enlargement of liver and spleen;

recurrent bronchitis, pharyngitis, and sinusitis; nocturnal sweats, elevated temperature in the evening, and considerable weakness;

diarrhea;

seborrhea-like skin inflammation;

white spots (candidiasis) in the mouth and esophagus;

loss of 13 kg in weight in the foregoing trimester, corresponding to 12% of his body weight;

Karnofsky status: 50%;

hemoglobin: 11.90 g/100 ml;

lymphocytes (total count): 690/mm$^3$;

CD4+ cells: 39/mm$^3$;

antigen p24 in the blood: present, at >200 U/ml.

Effects of l-acetylcarnitine a) Effects on general condition:

The general condition improved during the first 6 weeks of treatment, and the body weight became stabilized. The swellings of the lymph glands disappeared, as did the remaining symptoms, except for a slight enlargement of liver and spleen. The Karnofsky index rose to 80 after 12 weeks, and the patient returned to work. The patient has been going around doing his usual activities since then. He weighs about 90 kg.

b) Effects on total lymphocytes and CD4+ cells:

A constant decrease in total circulating lymphocytes and CD4+ cells was observed during the first 17 months of treatment. Total lymphocytes dropped to 390/mm$^3$ in the course of the seventh month, whereas CD4+ cells were no longer measurable.

After 17 months, the total lymphocytes were 178/mm$^3$, and CD4+ cells still could never be determined. However, a lymph cytic population of CD4+/CD8+ cells of 21/mm$^3$ appeared to be present. After 25 months, the total lymphocyte count was still 131/mm$^3$, and CD4+ cells could not be determined.

c) Effects on the p24-antigen level:

The p24 level was over 200 U/ml at the beginning of treatment. This situation remained unchanged for 12 months, but a decrease took place after that.

After 17 months of treatment, the p24 content was negative, whereas the level of p24 antibodies was elevated.

d) Effects on opportunistic infections:

Two episodes of white spots (candidiasis) in the mouth and esophagus occurred in the course of the treatment, which were successfully treated with Fluconazole (a fungicide), as well as an episode of an infection with *Pneumocistis carinii*, which was successfully treated with sulfamethoxazole and trimethoprim and was completely healed. A later diarrhea episode was also completely healed.

e) Toxicity and side effects:

No toxic and/or side effects which could directly or indirectly be linked to administration of the drug according to the invention were observed during the entire treatment period to date.

Case 2

45-year-old woman presenting with correlative AIDS complex (Walter Reed 4), who became infected as the sex partner of the above patient (Case 1), not given prior treatment, since she rejected treatment with AZT due to side effects appearing the first days of treatment and the effects on her partner. She consented to administration of the L-acetylcarnitine preparation by mouth at a dosage of 25 mg/kg/day for 17 consecutive months.

Infection probably occurred July, 1989. The primary HIV infection led to clinical determination of the similmononucleosis syndrome. The infection was determined in December, 1990.

The following clinical and laboratory situation was observed at the beginning of treatment:

bilaterally swollen lymph glands in the lateral and posterior cervical area, axillary region, and inguinal region;

periodic headaches with epistaxis;

nocturnal sweats, weariness, and inability to assume and maintain the supine position, which began following an episode of pulmonary inflammations;

repeated bladder inflammations and vulvovaginal white spots (candidiasis);

no loss of weight in the foregoing trimester;

Karnofsky status: 80%;

hemoglobin: 15.50 g/100 ml;

total lymphocytes: 2180/mm$^3$;

CD4+ cells: 252/mm$^3$;

blood p24 antigen: positive, but below 200 U/ml.

Effects of L-acetylcarnitine a) Effects on her general condition:

Her general condition was better during the first 12 weeks of treatment; her clinical symptomatology completely disappeared and did not reappear.

Her Karnofsky index rose to 100 and remained at that level.

b) Effects on total lymphocytes and CD4+ cells:

Both indexes began to rise in about the seventh month of treatment. The patient presented the following values in the twelfth month:

Total lymphocytes 2888/mmm$^3$

CD4+ 599/mm$^3$

After 25 months, these values were respectively 2480/mm$^3$ and 325/mm$^3$.

c) Effects on the p24-antigen level:

The content was already negative in the course of the twelfth week, and remained so. The antibody level was high.

d) Effects on opportunistic infections:

No infections of this type of any kind were observed.

e) Toxicity and side effects:

No toxic or side effects to be attributed directly or indirectly to administration of L-acetylcarnitine appeared during the entire treatment.

Large-scale trials are underway to confirm the above excellent effects of L-acetylcarnitine on physical complaints in AIDS.

In the trials described above, the active principle, L-acetylcarnitine, was administered together with excipients by mouth in the form of a loose powder mixture. However, the preparations may also be presented in other galetic forms and/or contain some other L-acylcarnitine as active principle and/or be combined with other pharmaceutical active principles.

We claim:

1. A method for treating physical symptoms of AIDS in a subject suffering from AIDS which comprises orally administering an amount of an L-acetylcarnitine to said subject effective to treat physical symptoms of AIDS wherein the L-acetylcarnitine is administered to the subject daily for a period of at least 12 weeks.

2. A method in accordance with claim 1 wherein the L-acetylcarnitine is administered at a dosage of 25–30 mg per kg of body weight per day.

3. A method in accordance with claim 1 wherein the L-acetylcarnitine is L-acetylcarnitine hydrochloride.

4. A method in accordance with claim 1 wherein the L-acetylcarnitine is administered daily for a period of at least 17 months.

5. A method in accordance with claim 1 wherein the L-acetylcarnitine is administered daily for a period of at least 25 months.

6. A method in accordance with claim 1 wherein said subject had previously been treated with AZT but such treatment had since been discontinued.

7. A method for treating physical symptoms of AIDS in a subject suffering from AIDS which comprises orally administering an amount of an L-acetylcarnitine to said subject effective to treat physical symptoms of AIDS wherein the L-acetylcarnitine is administered to the subject daily for a period of at least 12 weeks and wherein the subject has previously been treated with AZT but such treatment had since been discontinued.

* * * * *